US007169357B2

(12) United States Patent
Motegi et al.

(10) Patent No.: US 7,169,357 B2
(45) Date of Patent: Jan. 30, 2007

(54) AUTOMATIC CHEMICAL ANALYZER

(75) Inventors: Naoya Motegi, Hitachinaka (JP); Kiyotaka Saito, Hitachinaka (JP); Tomonori Mimura, Tomobe (JP)

(73) Assignees: Hitachi, Ltd., Tokyo (JP); Hitachi Science Systems, Co., Ltd., Ibaraki (JP)

( * ) Notice: Subject to any disclaimer, the term of this patent is extended or adjusted under 35 U.S.C. 154(b) by 342 days.

(21) Appl. No.: 09/934,482

(22) Filed: Aug. 23, 2001

(65) Prior Publication Data

US 2002/0076352 A1 Jun. 20, 2002

(30) Foreign Application Priority Data

Dec. 15, 2000 (JP) ............................. 2000-381160

(51) Int. Cl.
*G01N 21/01* (2006.01)
*G01N 33/50* (2006.01)

(52) U.S. Cl. ........................... 422/67; 422/63; 422/64; 422/65; 422/66; 436/43; 436/47; 436/48; 436/49; 436/50

(58) Field of Classification Search ............ 422/63–67; 436/43, 47–50
See application file for complete search history.

(56) References Cited

U.S. PATENT DOCUMENTS

| 4,276,051 | A | * | 6/1981 | Ginsberg et al. ............... 436/47 |
| 4,785,407 | A | * | 11/1988 | Sakagami ..................... 702/22 |
| 4,865,993 | A | * | 9/1989 | Cassaday ...................... 436/52 |
| 4,873,633 | A | * | 10/1989 | Mezei et al. .................. 356/39 |
| 4,971,913 | A | * | 11/1990 | Manabe et al. ................ 436/55 |
| 5,264,182 | A | * | 11/1993 | Sakagami ..................... 422/63 |
| 5,550,053 | A | * | 8/1996 | Salpeter ....................... 436/8 |
| 5,590,052 | A | * | 12/1996 | Kopf-Sill et al. ............ 700/266 |
| 5,635,364 | A | * | 6/1997 | Clark et al. .................. 435/7.92 |
| 5,948,358 | A | * | 9/1999 | Saito ........................... 422/64 |
| 6,146,592 | A | * | 11/2000 | Kawashima et al. ........... 422/67 |
| 6,509,192 | B1 | * | 1/2003 | Young ......................... 436/10 |

(Continued)

FOREIGN PATENT DOCUMENTS

EP            952452 A1      10/1999

(Continued)

*Primary Examiner*—Arlen Soderquist
(74) *Attorney, Agent, or Firm*—Mattingly, Stanger, Malur & Brundidge, P.C.

(57) ABSTRACT

According to the present invention, there is provided an automatic chemical analyzer which is capable of conducting investigation of the influence of contamination regardless of the knowledge or technical skill of the user, and can prevent the occurrence of errors of determination by letting the user know that a problem has arisen in the function of inhibiting the generation of contamination.

The combination of items which has been judged to involve contamination is extracted (step S7-1), and it is decided whether or not the result of judgement is the same as those of the previous judgements (step S7-2). In the step S7-2, if the results disagree, it is judged that trouble arises in the mechanism for preventing the generation of contamination, i.e., cleaning mechanism in this case, and an alarm of "trouble in cleaning mechanism" is given on the alarm display of a CRT.

Thus, the state of the apparatus can be monitored regardless of the technical skill of the user, and it is possible to prevent the errors of determination from occurring due to an abnormality in the state of the apparatus.

15 Claims, 6 Drawing Sheets

U.S. PATENT DOCUMENTS 6,635,488 B1 * 10/2003 Saito et al. .................. 436/43

FOREIGN PATENT DOCUMENTS

| JP | 59-040167 | 3/1984 |
| JP | 05-149955 | 11/1991 |
| JP | 5-149955 | 6/1993 |
| JP | 5-240867 | 9/1993 |
| JP | 7-270428 | 10/1995 |
| JP | 09-257803 | 3/1996 |

* cited by examiner

FIG. 5

| CODE | UNIT | LEVEL | ALARM MESSAGE | DATE,TIME |
|---|---|---|---|---|
| 013-006 | SAMPLE UNLOADER | STOP | RACK EXIT TRAY FULL | 00/10/13 17:07 |
| 007-001 | PC | WARNING | PRINTER ERROR | 00/10/13 17:13 |

DESCRIPTION,COUNTERMEASURE

CODE  : 013-006
LEVEL : STOP (DESCRIPTION AND REMEDY)
RACK CAN NOT BE COLLECTED ON RACK EXIT TRAYS DURING RESET.

(REMEDY)
PLACE THE RACK COLLECTION TRAY ON THE UNLOADER IN THE PROPER POSITION.
IF TRAY IS FULL, REPLACE WITH EMPTY TRAY.

[DELETE (L)]   [BUZZER (S)]   [MAINTENANCE (M)]   [CLOSE (C)]

FIG. 6

INPUT OF COTNAMINATION DETECTING CONDITIONS

REGISTRATION OF ITEMS OF ANALYSIS FOR DETECTION OF CONTAMINATION AND ALLOWANCE LIMIT

| ITEMS OF ANALYSIS | ALLOWANCE LIMIT |
|---|---|
|  |  |
|  |  |
|  |  |
|  |  |
|  |  |
|  |  |

REGISTRATION COMPLETED

FIG. 7

DETERMINATION WORK SHEET FOR JUDGEMENT ON PRESENCE OR ABSENCE OF CONTAMINATION

| SAMPLE NAME | POSITION | AMOUNT OF SAMPLE ($\mu l$) |
|---|---|---|
| SAMPLE FOR ITEM A | 1 | 180 |
| SAMPLE FOR ITEM B | 2 | 171 |
| DETERGENT | 3 | 170 |

AUTOMATIC CHEMICAL ANALYZER

BACKGROUND OF THE INVENTION

1. Field of the Invention

The present invention relates to an automatic chemical analyzer which is capable of determining the plural components of a sample by using the independent reagents for the respective components, and in which the sections of conducting transfer, mixing and determination of the reagents, samples and reaction solution being determined are shared in part or wholly.

2. Description of the Related Art

Analysis of the specific components of a sample is realized by using the reagents which react specifically with the respective components. In the automatic chemical analyzers, it is possible to make determination of the plural items of analysis simultaneously or in parallel with each other by using these different reagents.

However, in the case of an automatic analyzer in which the mechanism of dispensing the sample and reagents, the vessel for carrying out the reaction of the sample with the reagents, the mechanism of stirring the sample with the reagents, etc., are shared in conducting the determination of the plural items of analysis, there may take place an unintended reaction or reactions due to contamination of the respective reaction solutions and reagents, giving rise to errors in the results of determination.

For instance, in case a reagent used in the item of analysis A contains a substance (such as a reaction inhibitor or accelerator) which may participate in the reaction in the item of analysis B, and the determination of the item of analysis A and that of the item of analysis B are conducted successively, if the reagent used in the item of analysis A is contaminated with the reagent used in the item of analysis B, the reaction in the item of analysis A may be caused to start during and proceed simultaneously with the reaction in the item of analysis B, giving rise to errors in the analytical result.

In order to avoid this problem, it has been required for the user to examine beforehand the probability of influence of the contamination and to work out a determination system which can preclude the occurrence of contamination. For instance, a method has been used in which the analysis of item C is interposed between the analyses of item A and item B so that the analysis of item B will not be conducted immediately after the analysis of item A.

In the automatic chemical analyzers, on the other hand, contamination has been avoided by, for instance, a method in which the user previously registers the combinations of the items of analysis where contamination may occur so that the order of analysis is changed automatically, or by incorporating an expedient (such as cleaning with water or detergent) for inhibiting the occurrence of contamination. But it has been the user's obligation to conduct an investigation of the influence of contamination.

Also, when a new item (or items) of analysis is (are) added or the formulation is changed with introduction of a new system, it is necessary to conduct an investigation of the influence of contamination whenever such addition of item(s) or change of formulation is made. For conducting an investigation of the influence of contamination, it needs to set the conditions under which the contamination can actually occur, so that the user must be well acquainted with the operating program, etc., of the system and is required have a very high level of knowledge and technical skill.

Actually, however, most of the users are unable to implement setting of the determination conditions for the investigation of the influence of contamination and to make the analysis of the determination results. Thus, even though using an automatic chemical analyzer having a function to shun the influence of the registered contamination, it has been probable that the influence of contamination be not avoided in the analysis and the false result be reported.

The devices capable of collecting data on cross-contamination by the reagents with ease are disclosed in JP-A-5-240867, JP-A-7-270428, etc.

In JP-A-5-240867 is disclosed a system which memorizes an analysis request pattern with the order of analysis for checking cross-contamination by the reagent dispenser and cells in a predetermined number of channels, and assigns the channels to the respective items of analysis, allowing anyone to easily obtain data on cross-contamination by the reagents.

However, it is likely that an automatic chemical analyzer, in long-time use, would become unable to sufficiently perform its function to inhibit the generation of contamination due to accumulation of contaminants or trouble in the system, causing errors in the result of determination by the contamination which does not occur in the normal state.

In the existing circumstances, it is necessary to detect the change of the state of the apparatus by checking the apparatus or finding the false data of determination on the user's part, and the reliability of the analytical result depends on the user's faculty. Particularly, in case the trouble advances gradually, it is likely that the user fails to notice abnormity of the apparatus and the false determination result is accepted.

SUMMARY OF THE INVENTION

The object of the present invention is to realize an automatic chemical analyzer with which the user can investigate the influence of contamination regardless of his knowledge and technical skill, which analyzer memorizes the result of the investigation of influence of contamination, compares the newly determined investigation result with the results of the previous investigations, and when these results disagree, lets the user know the occurrence of trouble in the function to inhibit the generation of contamination. Thus, in the analyzer of the present invention, the state of the apparatus is always monitored to obviate the occurrence of any analytical error.

In order to attain the above object, the present invention provides:

(1) An automatic chemical analyzer capable of determining the plural components of a sample by using the independent reagents for the respective components, in which the sections of conducting transfer, mixing and determination of the reagents, samples and reaction solution being determined are shared in part or wholly, said analyzer having a function to set the determination conditions for judging whether contamination is present or not and to make automatic judgement of the combinations of the items involving contamination for preventing the occurrence of errors of determination due to contamination, and further characterized in that in order to prevent the occurrence of errors of determination due to the generation of new contamination by a change of the state of the apparatus, the analyzer judges whether contamination is present or not, memorizes its result, compares the result with those of the previous judgements, and when these results differ more than a certain degree, judges that the state of the apparatus has changed, and indicates it to the user.

(2) An automatic chemical analyzer capable of determining the plural components of a sample by using the independent reagents for the respective components, in which the sections of conducting transfer, mixing and determination of the reagents, samples and reaction solution being analyzed are shaped in part or wholly, said analyzer having a function to set the determination conditions for judging whether contamination is present or not and to make automatic judgement of the combinations of the items involving contamination for preventing the occurrence of errors of determination due to contamination, and further characterized in that in order to prevent the occurrence of errors of determination due to the generation of new contamination by a change of the state of the apparatus, the analyzer judges whether contamination is present or not, memorizes its result, makes judgement on the presence or absence of contamination in parallel with the sample analysis, compares the result with those of the previous judgements, and when these results differ more than a certain degree, judges that the state of the apparatus has changed, and indicates it to the user.

(3) A recording medium for recording the operation of an automatic chemical analyzer capable of determining the plural components of a sample by using the independent reagents for the respective components, in which the sections of conducting transfer, mixing and determination of the reagents, sample and reaction solution being determined are shared in part or wholly, and which has a function to set the determination conditions for judging the presence or absence of contamination and to make automatic judgement of the combinations of the items involving contamination for preventing the occurrence of errors of determination due to contamination, said recording medium having stored therein an operating program which, in order to prevent the occurrence of errors of determination due to the generation of new contamination by a change of the state of the apparatus, makes judgement on whether contamination is present or not, memorizes its result, compares the result with those of the previous judgements, and when these results differ more than a certain degree, judges that the state of the apparatus has changed, and indicates it to the user.

With the above mechanism, it is possible to realize an automatic biochemical analyzer with which the user can investigate the influence of contamination regardless of his degree of knowledge or technical skill, and which, in operation, memorizes the result of the investigation of the influence of contamination, compares the result of the newly conducted investigation with those of the previous investigations, and when these results of investigations differ, lets the user know that trouble has arisen in the function for inhibiting the generation of contamination, the state of the apparatus is monitored, thereby preventing the errors of determination from occurring due to such contamination.

BRIEF DESCRIPTION OF THE DRAWINGS

FIG. 5 is an alarm indication on the display in the event of occurrence of abnormity in an embodiment of the present invention.

FIG. 6 is a display indication of input of the contamination detecting conditions in an embodiment of the present invention.

FIG. 7 is a work sheet of the determination conditions for making judgement on the presence or absence of contamination in an embodiment of the present invention.

DETAILED DESCRIPTION OF THE INVENTION

The present invention is further illustrated with reference to the embodiments of the present invention, but it is to be understood that these embodiments are intended to be illustrative and not to be construed as limiting the present invention in any way. The embodiments of the present invention are described below by referring to the accompanying drawings.

Figure 4:
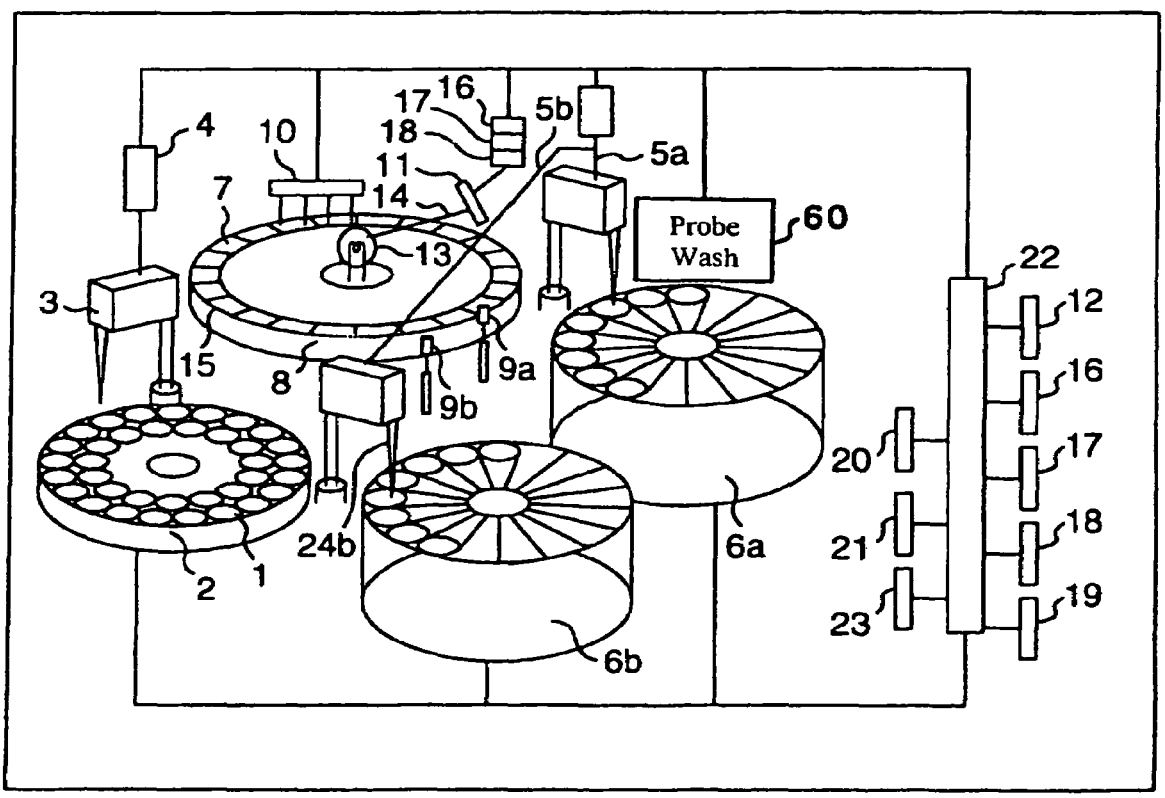
FIG. 4 is a schematic block diagram of an automatic chemical analyzer to which an embodiment of the present invention can be applied.

Referring to FIG. 4 of the accompanying drawings, there is shown a schematic block diagram of an automatic chemical analyzer embodying the present invention.

As shown in FIG. 4, this automatic chemical analyzer comprises a sample disc 2 on which a plurality of sample cups 1 can be installed and which is arranged turnable to the position of collection, a sampling mechanism 4 having a sample probe 3 for collecting a determined amount of a sample, reagent pipetting mechanisms 5a, 5b for pipetting the plural reagents, reagent discs 6a, 6b each carrying a plurality of reagent bottles and arranged turnable to the pipetting position, and a reaction disc 8 holding a plurality of reaction vessels 7 for direct photometry.

This automatic chemical analyzer is also provided with stirring mechanisms 9a, 9b, a reaction vessel cleaning mechanism 10, a photometer 11, and a central processor (microcomputer) 12 for controlling the whole system.

The reaction disc 8 holding a plurality of reaction vessels 7 is designed to be turnable to bring the reaction vessels 7 to the sample collecting position and the reagent pipetting position and to bring each vessel to a position on the optical axis of the photometer 11 for measuring absorbance of the reaction solution in the vessel.

The photometer 11, which is a multi-wavelength photometer having plural detectors, is disposed vis-à-vis to a light source lamp 13 so that when the reaction disc 8 is turning, a train of reaction vessels 7 will pass the light flux 14 from the light source lamp 13. A reaction vessel cleaning mechanism 10 is disposed between the position of light flux 14 and the position of sample discharge 15. The reaction vessels 7 are cleaned by this mechanism 10.

The automatic chemical analyzer of the instant embodiment is further provided with a multiplexer 16 for selecting the measuring wavelength, a logarithmic transformation amplifier 17, an A/D converter 18, a printer 19, a CRT 20, and a reagent pipetting mechanism drive circuit 21, which all are connected to a central processor 12 through an interface 22. This central processor 12 performs data processing such as control of the whole analyzer including control of the whole mechanical system and operation of density or enzyme activity.

The operating principle of the above automatic chemical analyzer is explained.

When the start switch on an operating panel 23 is turned on, cleaning of the reaction vessels 7 by the reaction vessel cleaning mechanism 10 is started, and measurement of water blank is made. The obtained value of this blank serves as a reference for the absorbance to be measured later with the reaction vessels 7.

When the reaction disc 8 makes one cycle of movement (half turn+movement through a distance for one vessel and temporary stop) to let a vessel advance to the sample discharge position 15, a sample cut 1 moves to the sampling position. At the same time, the two reagent discs 6a, 6b also move to the reagent pipetting position.

This synchronizes with the operation of sampling mechanism 4, and a sample (for example, a sample for the determination of item of analysis A) is sucked up from the sample cup 1 at the sampling position by a sample probe 3 and then discharged into the corresponding reaction vessel 7. Further, while a sample is being discharged into a reaction vessel 7 by the sampling mechanism 4, the reagent pipetting mechanism 5a is operated to let a reagent probe 24a suck up a first reagent for the item of analysis A placed at the corresponding position on the reagent disc 6a

Then the reagent probe 24a moves to a position above the specific reaction vessel 7 to discharge the reagent into this vessel, after which the probe 24a has its inner and outer walls cleaned in a probe cleaning tank 60 and stands by until a first reagent for the next item of analysis B is pipetted. Photometry is conducted after the first reagent has been added.

This photometry is carried out when a reaction vessel 7 crosses the light flux 14 with turn of the reaction disc 8. When the reaction disc 8 makes one turn and a movement through a distance corresponding to two reaction vessels after the first reagent has been added, the stirring mechanism 8a is actuated to stir the sample and the reagent. When the reaction vessel 7 advances to the second reagent pipetting position, which is reached after 25 turns and movement through a distance corresponding to 50 reaction vessels from the sample pipetting position, a second reagent is supplied from the reagent probe 24b and stirred by its stirring mechanism 8b.

With movement of the reaction disc 8, the reaction vessels 7 cross the light flux 14 one after another, and absorbance is measured each time a vessel crosses the light flux. For the determination of absorbance, photometry is conducted 50 times in total during the reaction time of 10 minutes. The reaction vessels 7 which have gone through photometry are cleaned by the reaction vessel cleaning mechanism 10 and left on standby until determination of the next sample is conducted. The determined absorbance is converted to density or enzyme activity by the central processor 12 and the analytical result is output from the printer 19.

In the event an abnormality occurs in the analyzer, it is automatically indicated on the display screen of CRT 20. For instance, as shown in FIG. 5, "alarm" indicating the occurrence of an abnormality is shown on the upper half of the screen (in the displayed information, "code" shows the code number of the alarm, "unit" indicates the location of occurrence of abnormality, and "level" indicates the degree of gravity of the alarm), and when "alarm" is selected, the remedy is shown on the lower half of the screen.

Figure 1:
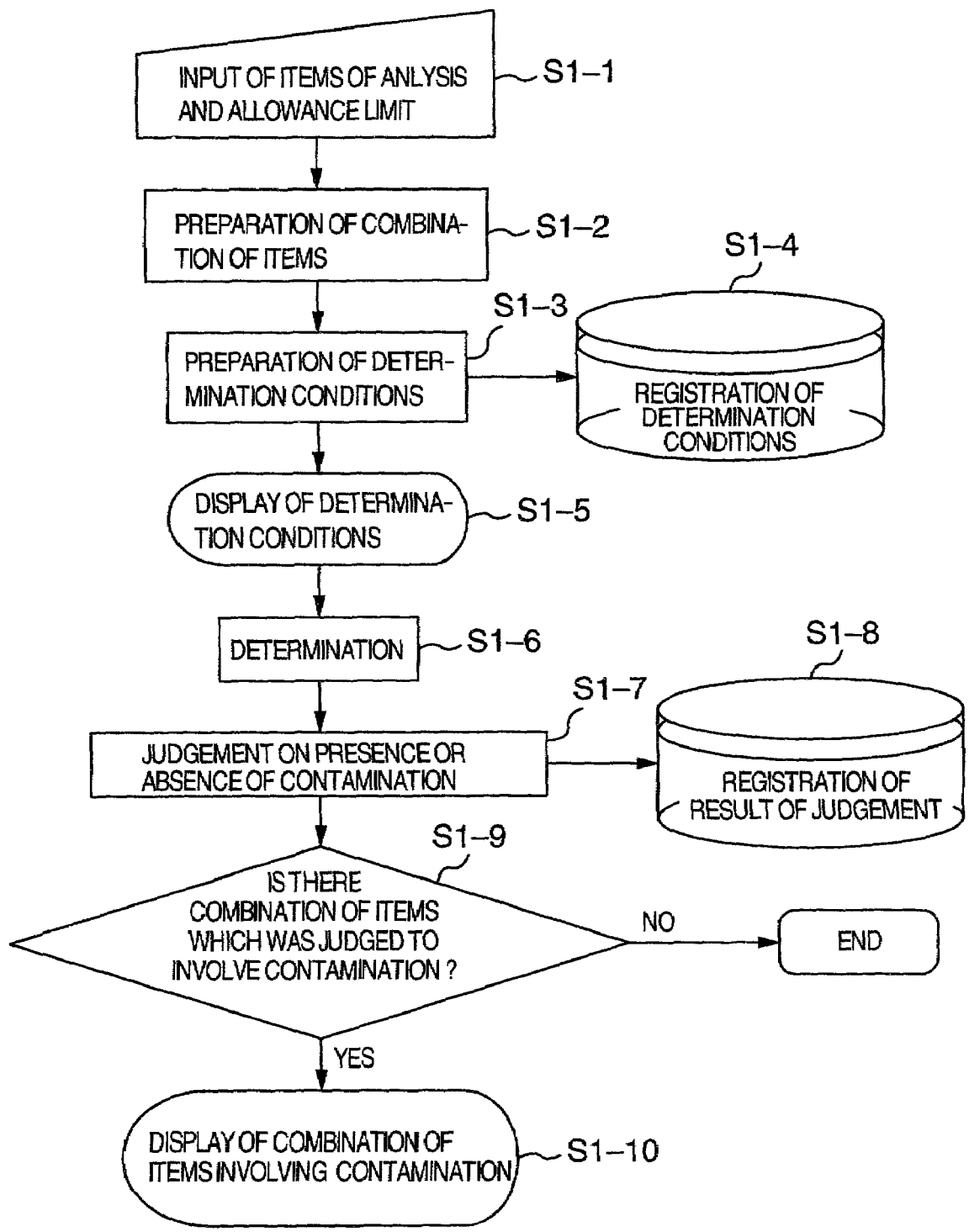
FIG. 1 is a flow chart showing the process of investigation of influence of contamination and decision of the evasion method in an embodiment of the present invention.

FIG. 1 is a flow chart showing the process of investigation of the influence of contamination and decision of the evasion method in the automatic chemical analyzer of the present invention.

In FIG. 1, when the item for making judgement on the presence or absence of contamination and the allowance limit serving as a criterion of judgement are input from the input/output section of the analyzer (step S1-1), a combination of items for conducting investigation of the influence of contamination from the input information is prepared according to the following formula (step S1-2).

From the items input in the step S1-1, there are prepared the combinations of the items which give influence and those which receive influence. For instance, in case the three items A, B and C are input in the step S1-1, there are prepared the following 6 combinations of the items giving influence→the items receiving influence:

A→B, A→C, B→A, B→C, C→A, C→B

The order of determination for obtaining the data necessary for making judgement on the presence or absence of contamination for each prepared combination is set according to the following formula (step S1-3) and memorized (step S1-4).

Regarding the order of determination, the combinations prepared in the step S1-2 are arranged in the order of the item giving influence and the item receiving influence for each combination, with all the combinations being arranged in this way successively. Then, as the combinations which do not receive influence, the same items are placed successively twice. For instance, in case the items of analysis are A, B and C and they were input in the order of A, B and C, the following order of determination is prepared: A→B→A→C→B→A→B→C→C→A→C→B→A→A→B→B→C→C The prepared order of determination and the disposed position of the sample are displayed on the screen (step S1-6).

Figure 2:
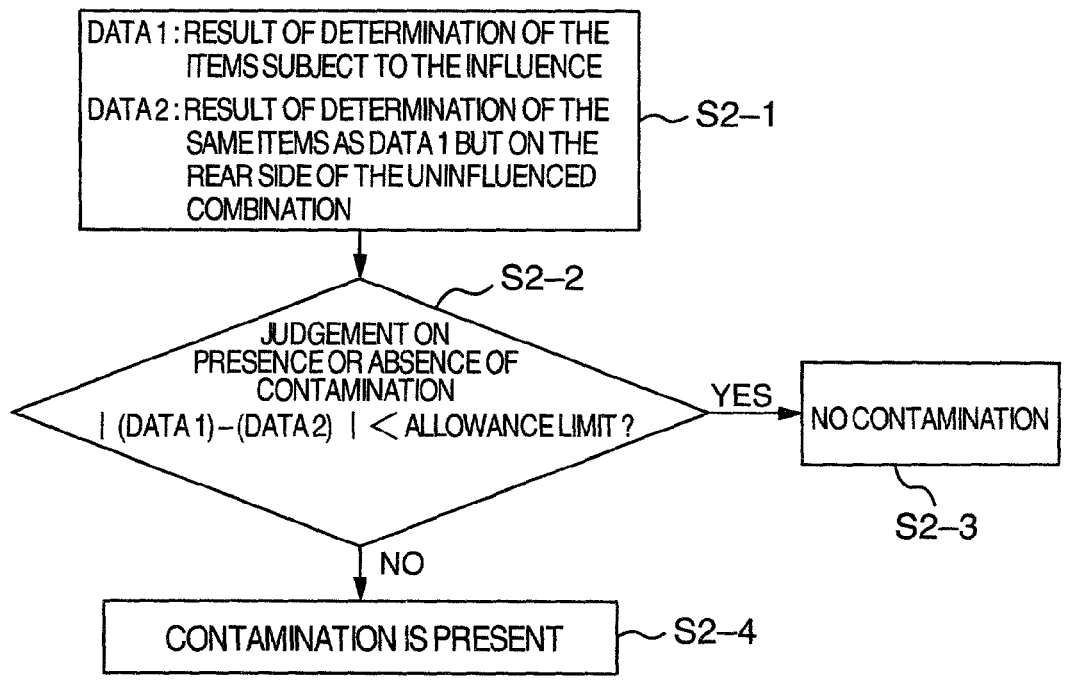
FIG. 2 is a flow chart showing a method of judging the presence or absence of contamination in an embodiment of the present invention.

One position of sample is allotted to each item of analysis. When a sample is set according to the output information and analyzed (step S1-7), judgement is made, based on the obtained result of analysis, over whether contamination is present or absent by the process shown in FIG. 2 (step S1-8) and the result of judgement is memorized (step S1-9).

In making judgement on the presence or absence of contamination, the following two data are extracted for each combination of items prepared in the step S1-2 (step S2-1):

Data 1: Result of determination of the influenced item

Data 2: Result of determination of the same item as Data 1 but on the rear side of the non-influenced combination Regarding the extracted data, judgement is made whether the following formula (1) holds or not (step S2-2).

$$|(data\ 1) - (data\ 2)| < allowance\ limit \quad (1)$$

When the above formula (1) holds, it is judged that there is no contamination (step S2-3), and when the above formula (1) does not hold, it is judged that there is contamination (step S2-4).

When there is a combination of items which was judged to have contamination, such a combination of items is indicated on the display (step S1-10)

By the above series of operations, setting of the determination conditions for judging contamination and judgement of the result can be made regardless of knowledge or technical skill of the user.

Automatic analyzers are usually provided with an expedient for inhibiting the occurrence of contamination, such as a cleaner system. Therefore, if some trouble or other arises in the analyzer to cause a change in the state of the contamination preventing mechanism, there is produced a corresponding change in the influence of contamination.

Figure 3:
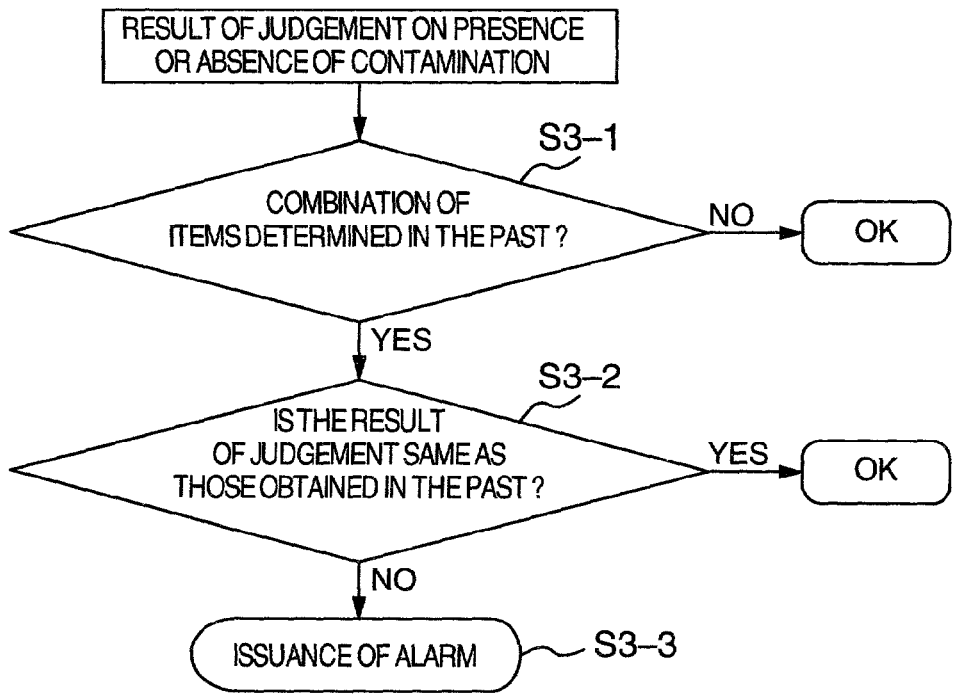
FIG. 3 is a flow chart showing a method of detecting trouble in the contamination evasion mechanism by judging the presence or absence of contamination in an embodiment of the present invention.

So, when investigating the influence of contamination, it is checked whether a similar investigation has been conducted with the same combination of items as shown in FIG. 3 (step S3-1), and the result of judgement is compared with that in the previous investigation (step S3-2).

In case a combination of items which has been judged to have no contamination before is now judged as having contamination, an alarm informing of the occurrence of trouble in the contamination preventing mechanism is issued (step S3-3).

Also, the combination of an item giving influence and an item receiving influence for making judgement on the presence or absence of contamination and the allowance limit for judgement are previously registered so that it is possible to make judgement on the presence or absence of contamination for the registered combination even in the ordinary analysis of the sample.

The interval of determination is also previously registered in the case of an analyzer which can be always loaded with the sample for making judgement on the presence of absence of contamination, allowing to conduct determination at the registered interval during the ordinary analysis of the sample. In the case of an analyzer incapable of always carrying the sample, determination is conducted at arbitrary intervals in the ordinary sample analysis by using a specific sample rack or other suitable means.

When the operation is carried out, judgement is made on the presence or absence of contamination, and when contamination is judged to be present, an alarm informing of the occurrence of trouble in the contamination evasion mechanism is issued as shown in FIG. 5.

Thus, it becomes unnecessary for the user to keep watch on the whole system throughout the operation, and it also becomes possible to prevent the determination errors from occurring from user's negligence of check-up.

Next, the operation of the present automatic biochemical analyzer when the items of analysis are two, A and B, is explained.

The display is switched to an indication of the input conditions for conducting an investigation of the influence of contamination by CRT 20 or operating panel 23. Such an input indication is exemplified in FIG. 6. In this indication, only the input information necessary for the investigation of the influence of contamination is displayed. The user has only to input item A as the item of analysis for conducting detection of contamination while also inputting the allowance limit for making judgement on the presence or absence of contamination. Item B is similarly input.

When input has been completed for all items, "registration completed" is entered, whereupon the analyzer prepares the combinations of items for judging the presence or absence of contamination. Since the items of analysis are A and B, there are prepared the following two combinations: A→B (combination 1) and B→A (combination 2).

Then, regarding these two combinations of items, the order of determination for obtaining data for making judgement on the presence or absence of contamination is decided and memorized. The order of determination for the combination 1 is B→A→B, and the order of determination for the combination 2 is A→B→A. For the continuous determination of the two combinations, the sequence of operation of B→A→B→cleaning→A→B→A is memorized.

Based on the memorized order of determination, the amounts of the sample and detergent used are calculated by multiplying the amount used per one operation by the number of times of determination of the sample or detergent and adding thereto the dead volume of the vessel, and the determined amounts are printed out along with the disposed positions of the sample and detergent at the time of determination, as a work sheet from the printer 19. There is used one sample for each item of analysis, and a detergent is used for cleaning. As for the disposed positions of the samples and detergent, they are placed in the order of the sample for item A, the sample for item B and the detergent, from position 1.

FIG. 7 shows an example of work sheet in case the amounts of the samples and detergent for one operation were as follows: sample for item A=10 μl; sample for item B=7 μl; detergent=20 μl. Following the instructions on the work sheet, the user sets the samples on the sample disc 2 and instructs start of the contamination detection operation from CRT 20 or operation panel 23.

The result of determination is sent to the central processor (microcomputer) 12 where judgement on the presence or absence of contamination is made. In making judgement on the presence or absence of contamination, the data involving no contamination and the data involving contamination are extracted for the respective items receiving contamination for each of the previously prepared combinations of items. The data used for the judgement in the result of determination are as follows:

Combination 1:
Data of item B involving no contamination . . . Data 1
Data of item B involving contamination . . . Data 2
Combination 2:
Data of item A involving no contamination . . . Data 3
Data of item A involving contamination . . . Data 4

Then the absolute value of the difference between the two data is determined for each combination and used as data for the judgement.

In an embodiment of the present invention, the following two data are determined:

Data for judgement of combination 1: |(Data 1)–(Data 2)|

Data for judgement of combination 2: |(Data 3)–(Data 4)|

Then these data for judgement are compared with the allowance limit, and when they exceed the allowance limit, it is judged that there exists contamination, and when they fall within the allowance limit, it is judged that there exists no contamination, and the result of judgement is registered in the central processor (microcomputer) 12.

For the combination of items which has been judged to involve contamination, its evasion method is prepared and registered in the central processor (microcomputer) 12. The evasion method comprises cleaning by a detergent between determination of the item giving influence and determination of the item receiving influence. For this method, the item giving influence, the item receiving influence and the amount of detergent used for the evasion of contamination are registered.

As for the amount of the detergent used, there is registered the same volume as the amount of the reagent registered in the analytical conditions of the item for analysis giving contamination which is memorized in the central processor (microcomputer) 12.

In an embodiment of the present invention, when it is judged that there exists contamination in the combination of A→B, the following matters are registered:

Item giving influence: item A

Item receiving influence: item B

Amount of detergent: amount of the reagent used in item A

In the determination of the sample, contamination is evaded according to the registered evasion method.

With the above mechanism, when the user registers the item of analysis demanding the investigation of influence of contamination and the allowance limit for judgement, the process to be followed, from detection of contamination till its evasion, is automatically prepared. Therefore, for any user who is capable of giving instructions from CRT 20 or operation panel 23, which is the knowledge of minimum requirement for the operation of the automatic chemical analyzer, it is possible to make the best use of the described functions of the apparatus and to easily obtain the determination results with high reliability.

Next, in case it has been judged that there was contamination in A→B in the investigation of influence of contamination by the above method, the judgement over whether an abnormality in the state of the apparatus has occurred or not and the ensuing operations are explained with reference to FIG. 8.

Figure 8:
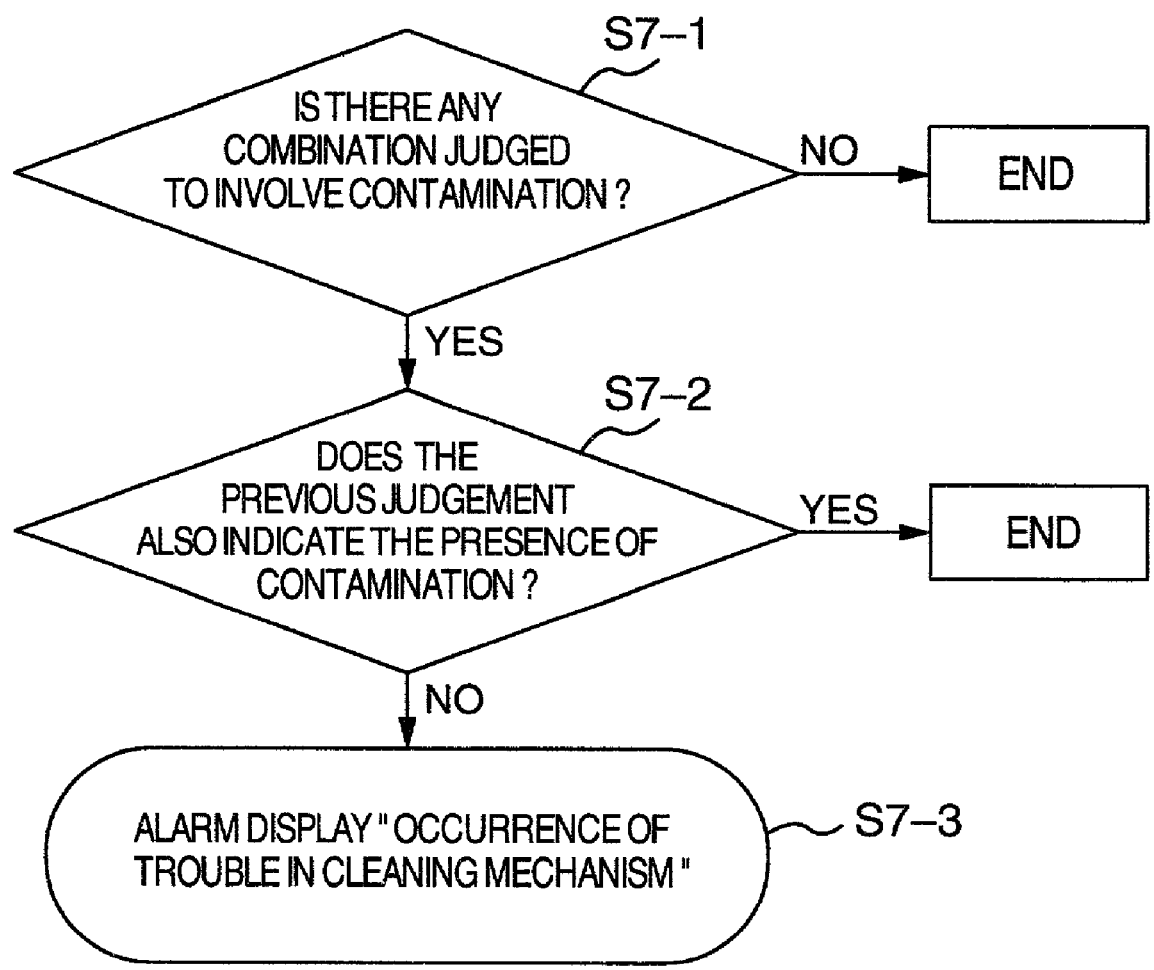
FIG. 8 is a flow chart showing a method of detecting trouble in the cleaning mechanism by judging the presence or absence of contamination in an embodiment of the present invention.

As shown in FIG. 8, the combination of items which has been judged to involve contamination is extracted (step S7-1), and it is decided whether or not the result of judgement is the same as those of the previous judgements (step S7-2).

In the step S7-2, if these results disagree, it is judged that trouble arose in the mechanism for preventing the generation of contamination, viz. cleaning mechanism in this case, and an alarm of "trouble in cleaning mechanism" is given on the alarm display of CRT 20 as illustrated in FIG. 5.

Thus, according to an embodiment of the present invention, the state of the apparatus can be monitored regardless of the technical skill of the user, and it is possible to prevent the errors of determination from occurring due to an abnormity in the state of the apparatus.

Operations in another embodiment of the present invention are described below.

For the ordinary analysis of a sample, judgement on the presence or absence of contamination for the designated combination of items is made, and the combination of items for determining the influence of contamination, the allowance limit for variation and the intervals of determination are registered from CRT 20 or operation panel 23.

In case the combination of A→B is input as the combination of items for determining the influence of contamination, designated combination 1 above, for each of the 50 samples at the registered determination intervals, determination of contamination for A→B is conducted in the order of determination, B→A→B between the 50th and the 51st sample in the ordinary determination of the samples.

The sample for judging the presence or absence of contamination is set at its own position on the sample disc 2. When the ordinary formula of sample determination is started in this state, determination for the judgement on the presence or absence of contamination is conducted at the designated intervals in the same way as in the above-described instance.

When it is judged that contamination is present, a corresponding alarm is issued, informing the user of a change in the state of the apparatus. This function makes it unnecessary for the user to keep watch on the apparatus throughout the operation and also prevents the occurrence of errors of determination due to user's negligence of check-up.

According to the present invention, as described above, there is provided an automatic chemical analyzer which is capable of conducting investigation of the influence of contamination regardless of the knowledge or technical skill of the user and can also prevent the occurrence of errors of determination by supervising the state of the apparatus as the present analyzer, in operation, memorizes the result of investigation of the influence of contamination, compares the newly obtained result with those of the previous investigations, and when these results disagree, lets the user know that trouble arose in the function of inhibiting the generation of contamination.

What is claimed is:

1. An automatic chemical analyzer capable of determining plural components of samples by using independent reagents for respective components of said samples, comprising a sampling mechanism having a sampling probe that dispenses the samples to reaction vessels and a mechanism for pipetting plural kinds of reagents with a same reagent pipetting probe from a reagent supply to the reaction vessels, said reaction vessels holding a reaction solution of said samples and said reagents that is analyzed, and a means for washing the reagent pipetting probe, and in order to prevent occurrence of errors of determination due to cross-contamination occurring among the reagents, the analyzer is provided with a control unit that functions to set determination conditions for judging the presence or absence of the cross-contamination occurring among the reagents and to make automatic judgment of the combination of items involving the cross-contamination, wherein in order to prevent the occurrence of errors of determination due to generation of new contamination by variation of the state of the washing means, the control unit makes judgment on the presence or absence of the cross-contamination for combinations of the reagents by testing a standard sample, memorizes the judgment result in relation to the reagent combinations, compares the judgment result with the judgment result of previously made judgments for the same reagent combinations; and when these results differ more than a predetermined amount, judges that the state of the washing means has changed, and indicates it to the user.

2. An automatic chemical analyzer according to claim 1, further including an input section to input the conditions for the judgment on the presence or absence of the cross-contamination or the predetermined amount of difference in judgment results used as a criteria for the judgment on the presence or absence of the cross-contamination occurring among the reagents.

3. An automatic chemical analyzer according to claim 1, further including an input section to register in advance the conditions for the judgment on the presence or absence of the cross-contamination or the predetermined amount of difference in judgment results used as a criteria for the judgment on the presence or absence of the cross-contamination occurring among the reagents and to judge the presence or absence of the cross-contamination occurring among the reagent combinations that have been registered in advance in parallel with the determinations of the components of the samples.

4. An automatic chemical analyzer according to claim 1, further including an input section to register an interval at which the presence or absence of the cross-contamination occurring among the reagents is determined in parallel with the determinations of the components of the samples.

5. An automatic chemical analyzer according to claim 1, further including an input section and a processor to register, in the processor, in relation to the reagent combinations, measurements of reagent(s) giving an influence, measurements of reagent(s) receiving the influence and the amount of the reagent(s) that are used when giving the influence, when said analyzer recognizes the presence of the cross-contamination occurring among the reagents.

6. An automatic chemical analyzer according to claim 1, further including an input section and a processor to register in the processor a procedure to be performed, when said analyzer recognizes the presence of the cross-contamination occurring among the reagents in relation to the reagent combinations, for preventing the cross-contamination occurring among the reagents of the reagent combinations.

7. An automatic chemical analyzer capable of determining plural components of samples by using independent reagents for respective components of said samples, comprising a sampling mechanism having a sampling probe that dispenses the samples to reaction vessels and a mechanism for pipetting plural kinds of reagents with a same reagent pipetting probe and means for washing the reagent pipetting probe from a reagent supply to the reaction vessels, said reaction vessels holding a reaction solution of said samples and said reagents that is analyzed, and in order to prevent the occurrence of errors of determination due to cross-contamination occurring among the reagents, the analyzer is provided with a control unit that functions to set determination conditions for judging the presence or absence of the cross-contamination occurring among the reagents and to make automatic judgment of the combination of items involving the cross-contamination, wherein in order to prevent the occurrence of errors of determination due to generation of new contamination by variation of the state of the washing means, the control unit makes judgment on the presence or absence of the cross-contamination for combinations of the reagents by testing a standard sample, memorizes the judgment results, conducts judgment on the presence or absence of the cross-contamination in parallel with the determination of components of the samples, compares the judgment result with the judgment result of previously made judgments for the same reagent combinations, and when these results differ more than a predetermined amount, judges that the state of the washing means has changed, and indicates it to the user.

8. An automatic chemical analyzer according to claim 7, further including an input section to input the conditions for the judgment on the presence or absence of the cross-contamination or predetermined amount of difference in judgment results used as a criteria for the judgment on the presence or absence of the cross-contamination occurring among the reagents.

9. An automatic chemical analyzer according to claim 7, further including an input section to register in advance the conditions for the judgment on the presence or absence of the cross-contamination or the predetermined amount of difference in judgment results used as a criteria for the judgment on the presence or absence of the cross-contamination occurring among the reagents and to judge the presence or absence of the cross-contamination occurring among the reagent combinations that have been registered in advance in parallel with the determinations of the components of the samples.

10. An automatic chemical analyzer according to claim 7, further including an input section to register an interval at which the presence or absence of the cross-contamination occurring among the reagents is determined in parallel with the determinations of the components of the samples.

11. An automatic chemical analyzer according to claim 7, further including an input section and a processor to register in the processor measurements of reagent(s) giving an influence, measurements of reagent(s) receiving the influence and the amount of the reagent(s) that are used when giving the influence, when said analyzer recognizes the presence of the cross-contamination occurring among the reagents.

12. An automatic chemical analyzer according to claim 7, further including an input section and a processor to register in the processor a procedure to be performed, when said analyzer recognizes the presence of the cross-contamination occurring among the reagents in relation to the reagent combinations, for preventing the cross-contamination occurring among the reagents of the reagent combinations.

13. A recording medium for recording operation of an automatic chemical analyzer capable of determining plural components of samples by using independent reagents for respective components of said samples, comprising a sampling mechanism having a sampling probe that dispenses the samples to reaction vessels and a mechanism for pipetting plural kinds of reagents with a same reagent pipetting probe from a reagent supply to the reaction vessels, said reaction vessels holding a reaction solution of said samples and said reagents that is analyzed and a means for washing the reagent pipetting probe, and in order to prevent occurrence of errors of determination due to cross-contamination occurring among the reagents, the analyzer is provided with a control unit that functions to set determination conditions for judging the presence or absence of the cross-contamination occurring among the reagents and to make automatic judgment of the combination of items involving the cross-contamination, wherein in order to prevent the occurrence of errors of determination due to generation of new contamination by variation of the state of the washing means, a processor performs an operation program according to which the control unit makes judgment on the presence or absence of the cross-contamination for combinations of the reagents by testing a standard sample, memorizes the judgment result in relation to the reagent combinations, compares the judgment result with the judgment result of previously made judgments for the same reagent combinations, and when the results differ more than a predetermined amount, judges that the state of the washing means has changed, and indicates it to the user.

14. An automatic chemical analyzer comprising a sample disc having sample cups containing samples to be analyzed, a reagent disc for carrying reagents, a reaction disc having reaction vessels, a sampling mechanism having a sampling probe that dispenses samples from the sample disc to the reaction vessels, a pipetting mechanism having a reagent probe for pipetting reagents from the reagent disc to the reaction vessels so that a reaction solution of samples and reagents is held in said reaction vessels, a means for washing the reagent pipetting probe, a photometer for measuring absorbance of a reaction solution in the reaction vessel, and a control unit for instructing and monitoring operations of said sample disc, said reagent disc, said reaction disc, said sampling mechanism, said pipetting mechanism, said washing means and said photometer, wherein determinations of plural components of a sample are determined by using independent reagents for the respective components, plural kinds of reagents are pipetted with said reagent pipetting probe, and in order to prevent occurrence of errors of the determinations due to cross-contamination occurring among the reagents, the control unit stores predetermined determination conditions for judging the presence or absence of the cross-contamination occurring among the reagents with respect to said determination conditions and makes an automatic judgment of the cross-contamination occurring among the reagents, wherein in order to prevent the occurrence of errors of determination due to the cross-contamination occurring among the reagents by variation of the state of the washing means, the control unit makes judgment on the presence or absence of the cross-contamination for combinations of the reagents used in succession by testing a standard sample, memorizes the judgment result in relation to combinations of the reagents used in succession, compares the result with previous judgments for the same combinations of the reagents used in succession; and when these results differ more than a certain degree, judges that the state of the washing means has changed, and indicates it to the user.

15. An automatic chemical analyzer according to claim 14, further including an input section to register an interval at which the presence or absence of the cross-contamination occurring among the reagents is determined in parallel with the determinations of the components of the samples.

* * * * *